United States Patent

Daikuzono

[11] Patent Number: 5,951,542
[45] Date of Patent: Sep. 14, 1999

[54] METHOD OF LASER TREATMENT FOR LIVING TISSUE AND TARGET TO BE USED THEREIN

[75] Inventor: Norio Daikuzono, Cincinnati, Ohio

[73] Assignee: S.L.T. Japan Co., Ltd., Tokyo, Japan

[21] Appl. No.: 08/625,313

[22] Filed: Apr. 1, 1996

[51] Int. Cl.⁶ ................................. A61B 17/36
[52] U.S. Cl. ............................. 606/9; 128/898
[58] Field of Search .............. 606/2, 9, 10, 13, 606/131; 607/88, 89, 94, 96; 424/639, 646; 128/700, 898

[56] References Cited

U.S. PATENT DOCUMENTS

| | | | |
|---|---|---|---|
| 5,199,870 | 4/1993 | Steiner et al. | |
| 5,226,907 | 7/1993 | Tankovich | |
| 5,325,877 | 7/1994 | Young et al. | 131/372 |
| 5,423,803 | 6/1995 | Tankovich et al. | 606/9 |
| 5,523,027 | 6/1996 | Otsuka | 252/589 |
| 5,631,002 | 5/1997 | Yagi et al. | 424/62 |
| 5,645,840 | 7/1997 | Lajoie et al. | 424/400 |
| 5,738,679 | 4/1998 | Daikuzono | |

FOREIGN PATENT DOCUMENTS 0 408 757 A1   3/1992   European Pat. Off. .

OTHER PUBLICATIONS

Japanse Patent No. XP 002071912—Abstract only.
European Patent No. 0 807 8505—Abstract only.

*Primary Examiner*—Linda C. M. Dvorak
*Assistant Examiner*—Rosiland Kearney
*Attorney, Agent, or Firm*—McDermott, Will & Emery

[57] ABSTRACT

The present invention relates to a target material which enables, for example, the blotch to be uniformly and efficiently irradiated with laser light for elimination thereof.

In order to modify the living tissue by being irradiated with laser light, the liquid target including laser light absorbing powders having a particle size of not larger than 40 μm, which are dispersed in a dispersing medium is applied on the surface of the living tissue. Then the surface of the tissue on which the target material is applied is irradiated with the laser light. The laser light causes the temperature of the target material to be elevated so that vaporization of the tissue occurs.

8 Claims, 5 Drawing Sheets

METHOD OF LASER TREATMENT FOR LIVING TISSUE AND TARGET TO BE USED THEREIN

TECHNICAL FIELD OF THE INVENTION

The present invention relates to a system for laser treatment of the living tissue and a target to be used therefor. The present invention is used for modifying the tissue, for example, for eliminating the blotch by applying a liquid target material on the living tissue surface, for example, the skin surface where the blotch exists and irradiating the target material applied area with laser light to modify the tissue.

BACKGROUND OF THE INVENTION

The blotch is the skin tissue on which melanism takes place. Various methods of eliminating the blotch have heretofore been known, including a method of chemically peeling the blotch area on which hydrogen peroxide is applied and a method of vaporization of the blotch area by being irradiated with laser light.

However, it is very difficult to completely eliminate the blotch by these methods. Although a method of eliminating the blotch by irradiating it with laser light has attracted attention owing to its future, a high power laser light L is required, which is impinged upon the surface of the tissue M since a high proportion of the impinged laser light will be scattered in a rearward direction. A high proportion of the laser light which has been penetrated into the tissue will be scattered therein, resulting in that there is a risk that the unwanted tissue other than the target tissue might be damaged. Since the distribution of the strength of the laser light is such that the laser light induces higher temperatures in a core of an optical fiber and lower temperatures in the periphery thereof, uniform vaporization of the tissue can not be achieved. Since identification of the laser light irradiation position depends only upon visual monitoring, failure of irradiation of some of the target area is liable to occur.

It is therefore an object of the present invention to uniformly and efficiently irradiate the entire of a target tissue with laser light.

SUMMARY OF THE INVENTION

The present invention provides a method of treating the living tissue by irradiating it with laser light, comprising the steps of: applying on the surface of the living tissue a liquid target material including laser light absorbing powders having a particle size of not higher than 40 $\mu$m and a dispersant in which said powders are dispersed so that the thickness of the applied film becomes not higher than 40 $\mu$m; and irradiating the target material area of the tissue with laser light. The entire of the target tissue can be uniformly and efficiently irradiated with the laser light.

It is preferable that the irradiation laser light is pulsed laser light.

The present invention further provides a target material which is applied on the living tissue for laser light irradiation treatment thereof, characterized in that said liquid target material includes laser light absorbing powders having a particle size of not higher than 40 $\mu$m, which are dispersed in water and alcohol.

Said target material may be added with a surface active agent having surface active characteristics.

Said laser light absorbing powders may be a material having a color selected from the group of carbon, manganese dioxide and iron oxides.

It is preferable that the laser light absorbing powders have a particle size not higher than 10 $\mu$m.

Said target material may include alcohol and water at ratios of 0.5 to 10 and 3 to 25 for the laser absorbing powders.

PREFERRED EMBODIMENT OF THE INVENTION

Now, the present invention will be described by way of an embodiment in which the blotch on the skin of the tissue M is eliminated with reference to drawings.

Figure 1:
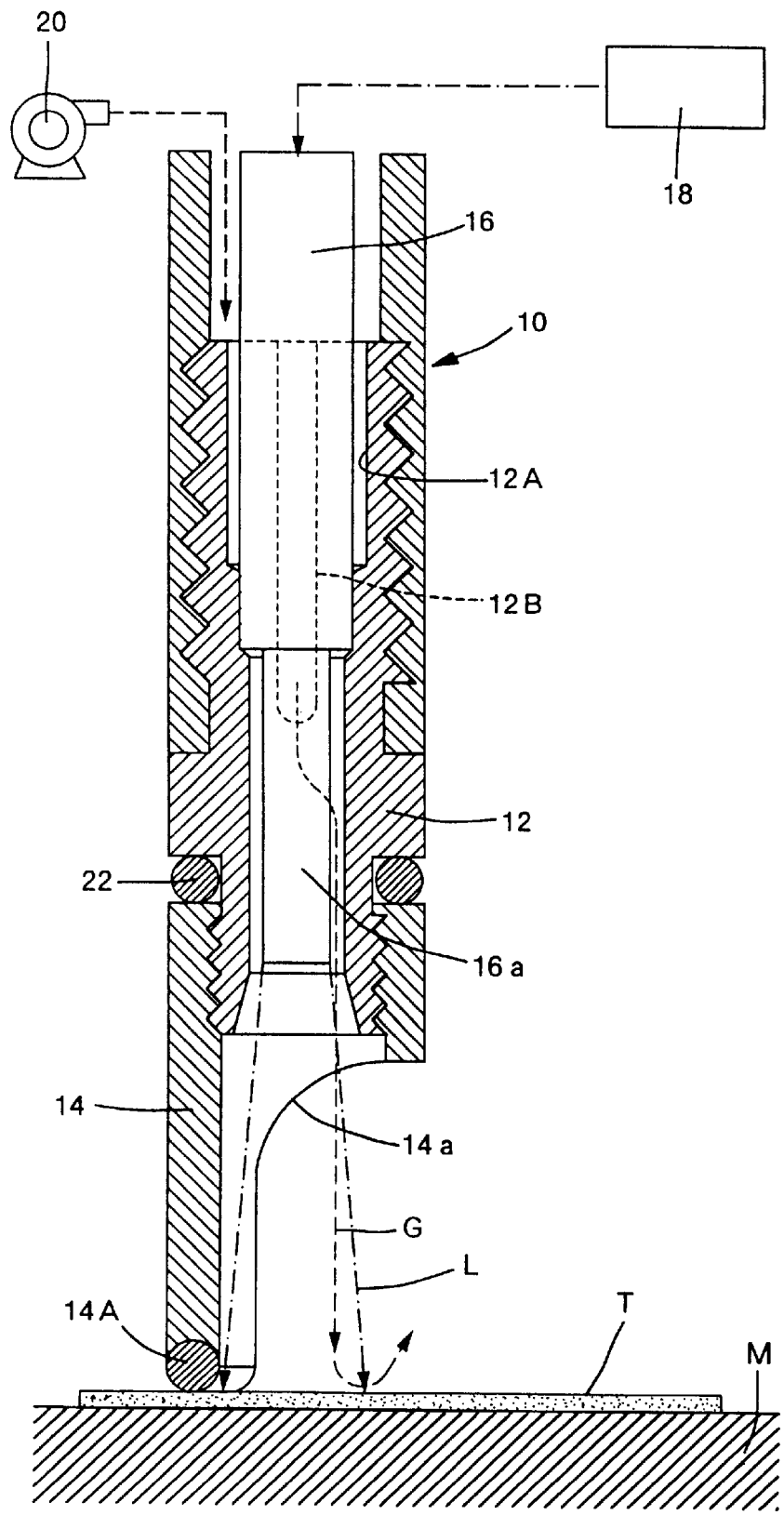
FIG. 1 is a schematic view showing an example of a laser light irradiating device of the present invention.
Figure 2:
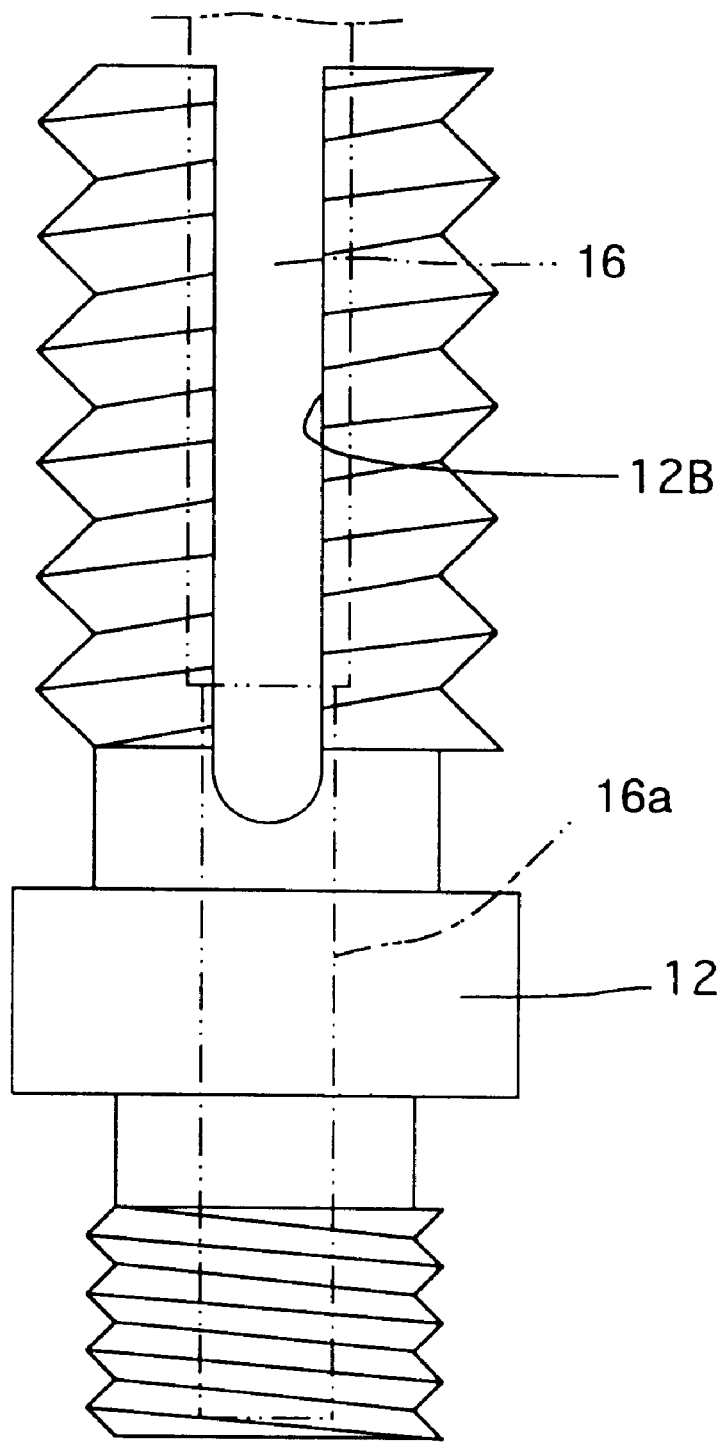
FIG. 2 is a front view showing a connector for the device shown in FIG. 1.

In the present invention, a connector 12 is threadably connected with the front end of a handpiece 10 (only the front end portion thereof is shown in FIG. 1) which is gripped by an surgical operator.

A distance keeping front terminal fitting 14 is threadably connected with the connector 12 at the front end thereof. A front end portion of an optical fiber 16 is inserted into a through-hole 12A of the connector 12 and is bonded thereto with an adhesive and the like. A clad is separated from the front end portion of the optical fiber 16 so that a core 16a is exposed. The connector 12 is formed with a notch 12B at the base thereof. The exposed core 16a is located in the notch 12B.

The optical fiber 16 is optically coupled with a laser light generator. The laser light generator 18 is preferably of capable of generating pulsed laser light. The handpiece 10 is supplied with a cooling gas such as cleaning gas or carbon dioxide from a compressed gas source 20. The gas G passes the notch 12B and a space between the inner surface of the through-hole 12A and the outer surface of the core 16a and then it is blown upon the target tissue M. Blowing of the gas is carried out for mitigating the burden upon a patient to be operated by removing the heat which is generated by the irradiation of the laser light L.

The front terminal fitting 14 is adapted to keep the distance between the laser light L emission tip end of the optical fiber 16 and the surface of the tissue M, for example the separation distance which falls within a range of 3 to 5 mm. In order to enable the operator to move the handpiece 10 to next position by sliding it along the surface of the tissue M, the metallic front terminal fitting 14 is integral with an abut guide 14A made of a plastic material having a circular cross-section and an arcuate longitudinal section, which is excellent in sliding characteristics. The front terminal fitting 14 is formed with an opening 14a having purposes of discharging the gas externally and of confirming the laser light irradiation position.

In the present invention, a target material is applied upon the surface of the tissue M. The target material includes laser light absorbing powders which are dispersed in a dispersant. The target material is liquid. The target material preferably includes laser light absorbing powders having a particle size of not higher than 40 μm, which are dispersed in water and alcohol.

The target material is applied on a target tissue, for example, the blotch to be eliminated with a felt pen. The laser light L which has transmitted through the optical fiber 16 from the laser light generator 18 is emitted toward the target applied area from the front end of the optical fiber.

The laser light L which has collided with the target material T will be absorbed by the laser light absorbing powders contained in the target material T so that it will be converted into thermal energy. As a result, the temperature of the laser light irradiated tissue elevates momentarily to high temperatures such as 800 to 1000 C, so that vaporization of the tissue takes place. If the vaporization of the tissue is not sufficient by one shot of the laser light, irradiation of the laser light is conducted again (after application of the target material). The number of repetitions of application of the target material and the laser light irradiation can be properly selected.

In order to enable the operator to conduct treatment while visually monitoring the manner of irradiation of the target material T with the laser light, an O-ring 22 is provided between the base end of the front terminal fitting 14 and a flange of the connector 12, which serves to stably secure the front end fitting 14 relative to the connector 12 after the angular position of the front terminal fitting 14 around its axis has been adjusted.

The target material includes laser light absorbing powders having a particle size of not larger than 40 μm, more preferably 10 m. If the particles size becomes larger, it is more difficult to properly disperse the powders in a dispersing medium and the film of the applied target material will have a larger thickness and a smooth surface of the film is not obtained, resulting in ununiform vaporization of the tissue on irradiation with laser light.

The dispersing agent may include water, in particular sterilized water. It is preferable to add the dispersing medium with alcohol. The alcohol may include methyl alcohol, ethyl alcohol, propyl alcohol, butyl alcohol. Addition of the alcohol enables the target material to be prematurely dried when the target material is irradiated with laser light since the alcohol is vaporized so that latent heat is removed due to vaporization. The dispersing medium may be added with anionic, nonionic, cationic surface-active agents as well as soap, such as pulverized medical soap in order to increase the dispersion properties. The surface-active agent or soap will provide an effect that the target material can be applied on the tissue to form a uniform film.

The laser light absorbing powders are not limited as far as they absorb the laser light to generate heat. The powder material may include carbon, manganese dioxide and iron oxides and a combination thereof. Since these material can be applied to a desired position on the surface of the tissue while visually monitored and the laser irradiation point on the target can be confirmed.

Figure 3:
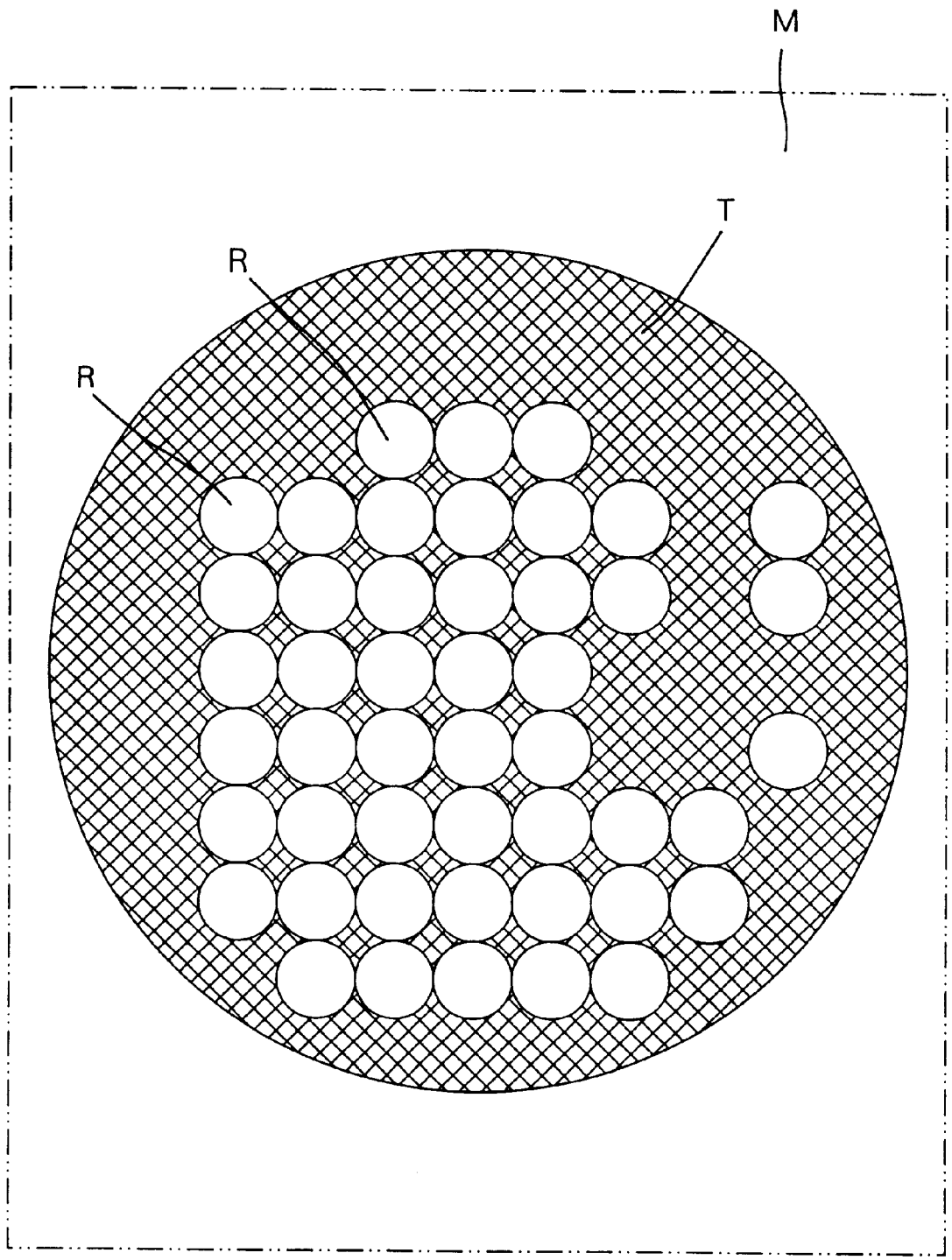
FIG. 3 is an explanatory view showing the relation between the target material applied area and the laser light irradiated area.
Figure 4:
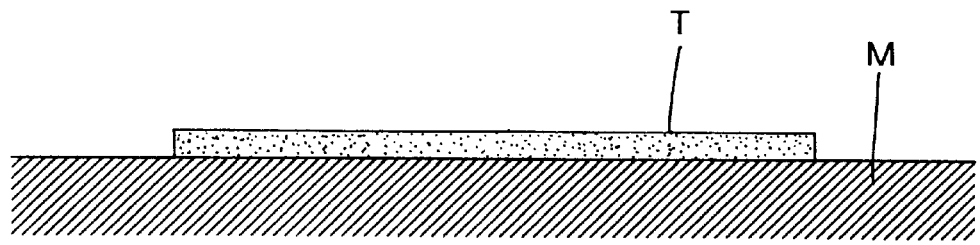
FIG. 4 is a schematic view showing the application condition of the target material.
Figure 5:
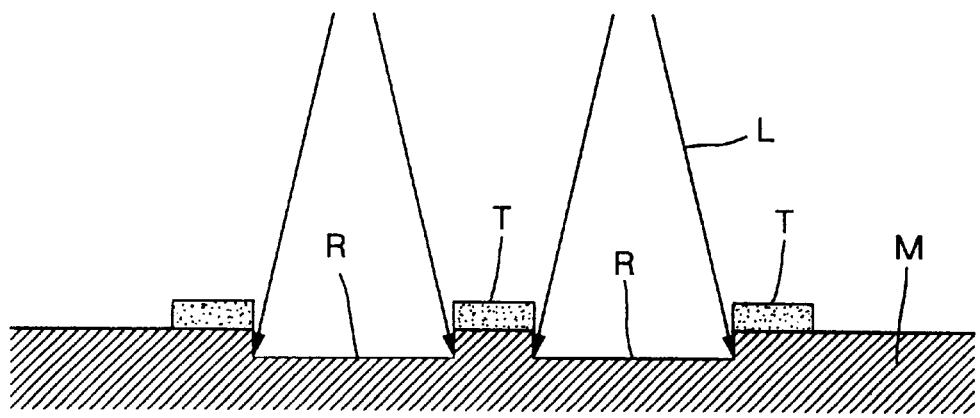
FIG. 5 is a schematic view showing the first laser light irradiated condition.
Figure 6:
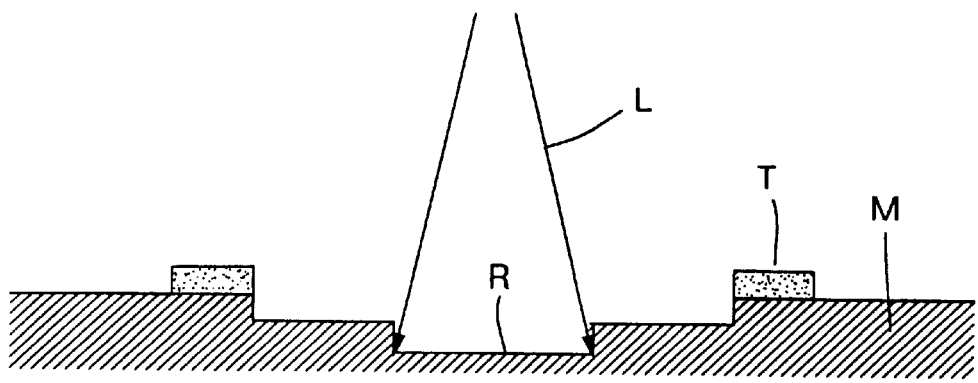
FIG. 6 is a schematic view showing the second laser light irradiated condition.
Figure 7:
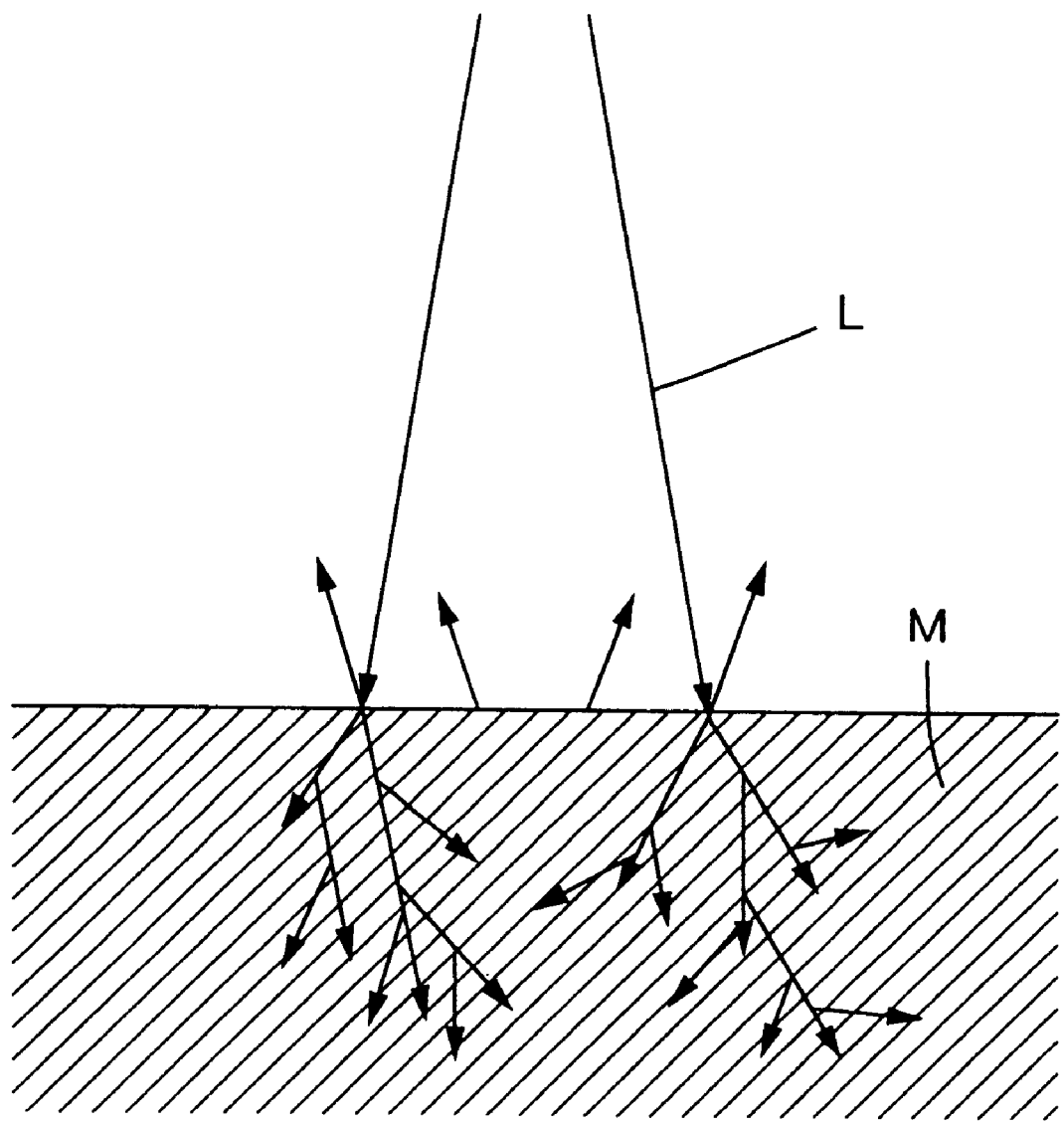
FIG. 7 is an explanatory view the condition of the scattering of the laser light without using any target material.

As shown in FIGS. 3 and 4, the target material T is applied on a given position on the tissue. The entire of the target T is irradiated with the laser light. The original skin condition can be viewed at the irradiated spots while the target material which has black color remains at the unirradiated spots as shown in FIGS. 3 and 5. An operator can determine that the black area has not been irradiated and then conduct laser light irradiation of the black area at next stage as shown in FIG. 6. This enables the operator to easily conduct the laser light irradiation over the entire of the desired area.

The liquid target may include alcohol, water and laser light absorbing powders in the following ratios:

(laser light absorbing powders):(alcohol):(water)=(1):(0.5–10):(3–25). The liquid target may have a viscosity of 2 to 200 CPS (20° C.). It is preferable that the liquid target have approximately same viscosity as that of milk to provide uniformity of the film.

Use of Nd:YAG laser light is more preferable than that of carbon dioxide gas laser light. It is preferable that the laser light be pulsed laser light having a pulse interval of 5 to 50 PPS at 10 to 500 mJ.

Although the present invention has been described by way of example of elimination of the blotch on the skin, it may be applied for discoloring of tatoo and elimination of skin lines as well as treatment of athlete's foot. In the field of surgery the target is applied on the dental tissue to achieve the removal of that portion.

What is claimed is:

1. A method of treating living tissue by heating a surface portion thereof with laser light, comprising the steps of:

applying on a surface of the surface portion of the living tissue a film of a liquid target material, including a laser light absorbing material having particles of a particle size of not higher than 40 μm, and a dispersant in which said particles are dispersed, a thickness of the applied film is not higher than 40 μm; and irradiating the target material film disposed outside the living tissue with laser light, all said laser light absorbing material remaining outside the living tissue during the entire time the living tissue is treated by irradiating of the target material film with laser light, energy of the laser light being absorbed in the laser light absorbing material applied on the surface of the surface portion of the living tissue to generate temperatures which vaporize the underlying surface of the surface portion of the living tissue to which the target material is applied, the particle size of the laser absorbing material resulting in only vaporization of the particles when subject to laser light, and no particle explosion.

2. The method according to claim 1, wherein:

the laser light is pulsed during said irradiation of the target material on the surface portion.

3. A target material for application on a surface of living tissue for laser light irradiation treatment thereof on said surface, characterized in that said target material is a liquid and includes a laser light absorbing material having a particle size not higher than 40 μm and which is dispersed in water and alcohol, all said laser light absorbing material remaining on the surface of the living tissue the entire time the living tissue is treated by laser light irradiation of the laser light absorbing material, absorbing energy of the laser light to generate temperatures which vaporize the underlying living tissue to which the target material is applied, the particle size of the laser absorbing material resulting in only vaporization of the particles when subject to laser light, and no particle explosion.

4. The target material according to claim 3, further comprising:

a surface active agent having surface active characteristics.

5. The target material according to claim 3, wherein:

said laser light absorbing material comprises a material selected from the group of materials consisting of carbon, manganese dioxide and iron oxides.

6. The target material according to claim 3, wherein:
the laser light absorbing material has a particle size not higher than 10 $\mu$m.

7. The target material according to claim 3, wherein:
said target material includes alcohol and water in ratios of 0.5 to 10 and 3 to 25 for the laser absorbing powders.

8. A method of treating a surface of a living tissue by laser light irradiation, comprising the steps of:

temporarily applying on the surface of the living tissue a liquid target material which includes a laser light absorbing powder having a particle size not higher than 40 $\mu$m and a dispersant in which said powder is dispersed so that the applied target material forms a film on said surface of a thickness not higher than 40 $\mu$m; and irradiating the applied target material with laser light, all the laser light absorbing powder remaining outside of the living tissue during the entire time the living tissue is treated by irradiating the applied target material with laser light, and energy of the laser light being absorbed in the laser light absorbing powder applied on the surface of the living tissue to generate temperatures which vaporize the underlying living tissue to which the target material is applied, the particle size of the laser absorbing powder resulting in only vaporization of the particles when subject to laser light, and no particle explosion.

* * * * *